United States Patent
Sayler et al.

(10) Patent No.: US 9,746,423 B2
(45) Date of Patent: Aug. 29, 2017

(54) REVERBERATION CHAMBER LOADING

(71) Applicant: ETS-Lindgren Inc., Cedar Park, TX (US)

(72) Inventors: Bryan Howard Sayler, Georgetown, TX (US); Michael David Foegelle, Cedar Park, TX (US); Garth Anthony D'Abreu, Austin, TX (US)

(73) Assignee: ETS-LINDGREN INC., Cedar Park, TX (US)

( * ) Notice: Subject to any disclaimer, the term of this patent is extended or adjusted under 35 U.S.C. 154(b) by 408 days.

(21) Appl. No.: 14/278,712

(22) Filed: May 15, 2014

(65) Prior Publication Data

US 2014/0338471 A1  Nov. 20, 2014

Related U.S. Application Data

(60) Provisional application No. 61/823,604, filed on May 15, 2013.

(51) Int. Cl.
| | |
|---|---|
| *G01N 21/88* | (2006.01) |
| *G01R 29/08* | (2006.01) |
| *G01N 29/00* | (2006.01) |
| *G01N 21/47* | (2006.01) |

(52) U.S. Cl.
CPC ....... *G01N 21/8806* (2013.01); *G01N 21/474* (2013.01); *G01N 29/00* (2013.01); *G01R 29/0821* (2013.01); *G01N 2021/8812* (2013.01); *G01N 2201/0631* (2013.01); *Y10T 29/49716* (2015.01)

(58) Field of Classification Search
None
See application file for complete search history.

(56) References Cited

U.S. PATENT DOCUMENTS

| | | | |
|---|---|---|---|
| 2,364,371 A |  | 12/1944 | Katzin |
| 2,425,250 A | * | 8/1947 | Lamb .................... G01R 11/04 |
| | | | 116/206 |
| 2,431,962 A |  | 12/1947 | Rettinger |
| 2,520,602 A |  | 8/1950 | Linder |
| 2,720,629 A |  | 10/1955 | Edson et al. |
| 2,735,507 A | * | 2/1956 | Vogel .................... D06F 58/22 |
| | | | 34/80 |

(Continued)

FOREIGN PATENT DOCUMENTS

| | | | |
|---|---|---|---|
| FR | 2700186 | * | 7/1995 |
| WO | 2012171562 A1 |  | 12/2012 |

OTHER PUBLICATIONS

Jesch—"Measurement of Shielding Effectiveness of Cable and Shielding Configurations by Mode-Stirred Techniques", IEEE Transactions on Electromagnetic Compatibility, vol. 30, No. 3, pp. 222-228, Aug. 1988.

(Continued)

*Primary Examiner* — Robert R Raevis
(74) *Attorney, Agent, or Firm* — Christopher & Weisberg, P.A.

(57) ABSTRACT

A method and system for selectively varying the performance of a test chamber are disclosed. According to one aspect, the performance is affected by a variable absorbing structure of the test chamber. The absorbing structure enables selective exposure of absorbing material to achieve a specific performance.

11 Claims, 8 Drawing Sheets

(56) References Cited

U.S. PATENT DOCUMENTS

| | | | |
|---|---|---|---|
| 2,849,828 A * | 9/1958 | Johnson | A01K 97/04 |
| | | | 220/212.5 |
| 3,281,728 A | 10/1966 | Dorne | |
| 3,745,226 A | 7/1973 | Nichols et al. | |
| 3,806,943 A | 4/1974 | Holloway | |
| 4,013,861 A | 3/1977 | Westfall | |
| 4,463,324 A | 7/1984 | Rolfs | |
| 4,494,117 A | 1/1985 | Coleman | |
| 4,513,290 A | 4/1985 | Lefevre et al. | |
| 4,733,165 A | 3/1988 | Richardson et al. | |
| 4,794,218 A | 12/1988 | Nakano et al. | |
| 4,906,998 A | 3/1990 | Shibuya | |
| 4,912,741 A | 3/1990 | Tanaka et al. | |
| 4,968,983 A | 11/1990 | Maeda | |
| 4,972,191 A | 11/1990 | Ishino et al. | |
| 5,001,494 A | 3/1991 | Dorman et al. | |
| 5,012,041 A | 4/1991 | Sims et al. | |
| 5,023,594 A | 6/1991 | Wallace | |
| 5,110,216 A | 5/1992 | Wickersheim et al. | |
| 5,134,405 A | 7/1992 | Ishihara et al. | |
| 5,215,959 A | 6/1993 | Van Duzer | |
| 5,300,939 A | 4/1994 | Maeda et al. | |
| 5,327,091 A | 7/1994 | Loughry | |
| 5,530,412 A | 6/1996 | Goldblum | |
| 5,805,667 A | 9/1998 | Alvarez et al. | |
| 5,874,715 A | 2/1999 | Choi | |
| 5,877,479 A | 3/1999 | Yu | |
| 6,070,662 A | 6/2000 | Ciglenec et al. | |
| 6,172,650 B1 | 1/2001 | Ogawa et al. | |
| 6,181,136 B1 | 1/2001 | Choi et al. | |
| 6,201,955 B1 | 3/2001 | Jasper et al. | |
| 6,597,723 B1 | 7/2003 | Zeira et al. | |
| 6,686,818 B1 | 2/2004 | Weibler et al. | |
| 6,850,851 B1 | 2/2005 | Fourestie et al. | |
| 7,228,105 B2 | 6/2007 | Rowell et al. | |
| 7,325,656 B2 * | 2/2008 | Oberer | B66B 13/285 |
| | | | 181/198 |
| 9,276,325 B2 * | 3/2016 | Sim | H01Q 17/00 |
| 2006/0055592 A1 | 3/2006 | Leather et al. | |
| 2010/0047405 A1 * | 2/2010 | Versteylen | A47J 47/10 |
| | | | 426/124 |
| 2013/0106639 A1 * | 5/2013 | He | G01R 29/0821 |
| | | | 342/1 |

OTHER PUBLICATIONS

Hatfield—"Shielding Effectiveness Measurements Using Mode-Stirred Chambers: A Comparison of Two Approaches", IEEE Transactions on Electromagnetic Compatibility, vol. 30, No. 3, pp. 229-238, Aug. 1988.

Hill—"Electronic Mode Stirring for Reverberation Chambers", IEEE Transactions on Electromagnetic Compatibility, vol. 36, No. 4, pp. 294-299, Nov. 1994.

Hill—"Spatial Correlation Function for Fields in a Reverberation Chamber", IEEE Transactions on Electromagnetic Compatibility, vol. 37, No. 1, p. 138, Feb. 1995.

Harms et al.—"Simulating Measurements for a Cable Radiation Study", IEEE Transactions on Electromagnetic Compatibility, vol. 38, No. 1, pp. 25-30, Feb. 1996.

Mitra et al.—"Power Transfer Characteristics of a Microwave Reverberation Chamber", IEEE Transactions on Electromagnetic Compatibility, vol. 38, No. 2, pp. 197-200, May 1996.

Herke et al.—"The Use of Mode Stirred Chambers in EM Evaluation Testing", 10th International Conference on Electromagnetic Compatibility, pp. 193-198, Sep. 1997.

Kwon et al.—"Ray Analysis of Electromagnetic Field Build-Up and Quality Factor of Electrically Large Shielded Enclosures", IEEE Transactions on Electromagnetic Compatibility, vol. 40, No. 1, pp. 19-26, Feb. 1998.

Hatfield et al.—"Investigations to Extend the Lower Frequency Limit of Reverberation Chambers", pp. 20-23, 1998.

Freyer et al.—"Verification of Fields Applied to an EUT in a Reverberation Chamber Using Statistical Theory", pp. 34-38, 1998.

Goldsmith et al.—"Design, Construction, Computational EM Modelling, and Characterisation of an Aircraft Sized Reverberation Chamber and Stirrer", pp. D55-1-D55-8, 1998.

Leferink—"High Field Strength in a Large Volume: The Intrinsic Reverberation Chamber", Hollandse Signaalapparaten B.V. Environmental Test Laboratory, pp. 24-27, 1998.

Slattery et al.—"Characterization of a Reverberation Chamber for Automotive Susceptibility", pp. 265-269, 1998.

Lehman et al.—"Verification of Fields Applied to an EUT in a Reverberation Chamber Using Numerical Modeling", pp. 28-33, 1998.

Hill—"Electromagnetic Theory of Reverberation Chambers", United States Department of Commerce, Technology Administration, National Institute of Standards and Technology, NIST Technical Note 1506, pp. 1-55, Dec. 1998.

Bunting et al.—"A Two-Dimensional Finite-Element Analysis of Reverberation Chambers", IEEE Transactions on Electromagnetic Compatibility vol. 41, No. 4, pp. 280-289, Nov. 1999.

Petirsch et al.—"Investigation of the Field Uniformity of a Mode-Stirred Chamber Using Diffusors Based on Acoustic Theory", IEEE Transactions on Electromagnetic Compatibility, vol. 41, No. 4, pp. 446-451, Nov. 1999.

Svetanoff et al.—"Development of High Performance Tuners for Mode-Stirring and Mode-Tuning Applications", pp. 29-34, 1999.

Harima et al.—"FDTD Analysis on the Effect of Stirrers in a Reverberation Chamber", Yokosuka Radio Communications Research Center, Communications Research Laboratory, M.P.T., pp. 260-263.

Lehman et al.—"Characterization of the Maximum Test Level in a Reverberation Chamber", Science & Engineering Associates, Inc., Albuquerque, NM 87110, USA, pp. 44-47.

Hatfield, et.al., "Frequency Characterization of Reverberation Chambers", Electromagnetic Compatibility, 1996, pp. 190-193, Symposium Record. IEEE 1996 International Symposium, Aug. 19-23, 1996.

Mitra, et.al., "Statistical Simulations and Measurements Inside a Microwave Reverberation Chamber." Electromagnetic Compatibility, 1997, pp. 48-53, IEEE 1997 International Symposium, Aug. 18-22, 1997.

Hatfield, et. al., "Reverberation Characteristics of a Large Welded Steel Shielded Enclosure", Electromagnetic Compatibility, 1997, pp. 38-43, IEEE 1997 International Symposium, Aug. 18-22, 1997.

* cited by examiner

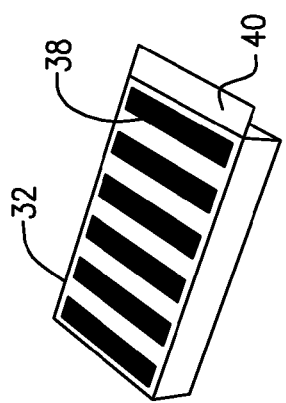
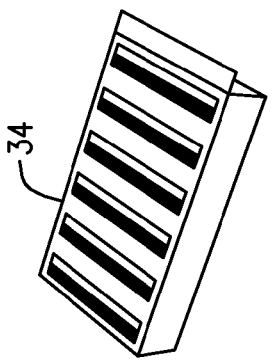
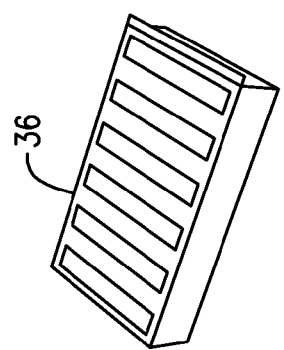
FIG. 3
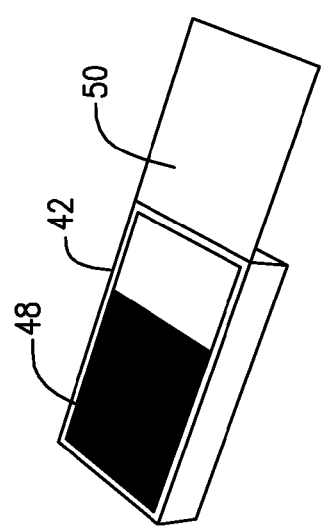
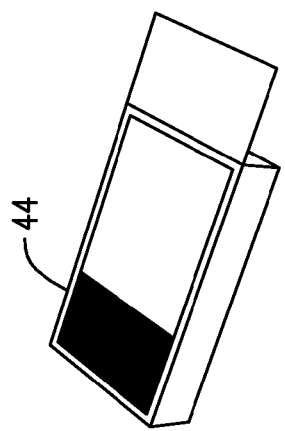
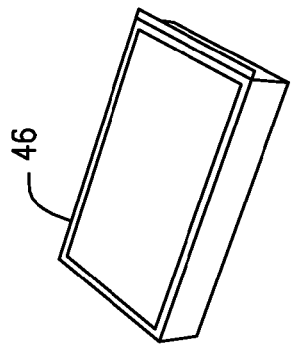
FIG. 4

REVERBERATION CHAMBER LOADING

CROSS-REFERENCE TO RELATED APPLICATION

This application claims priority of U.S. Provisional Application No. 61/823,604, filed on May 15, 2013, entitled "REVERBERATION CHAMBER LOADING" and which is incorporated herein in its entirety by reference.

FIELD

The present description relates to a method and system for variable, controllable, and repeatable loading of a reverberation chamber.

BACKGROUND

Reverberation chambers are used for generating statistically uniform and isotropic distributions of electromagnetic or acoustic energy within a test volume. In an electromagnetic reverberation chamber, the walls, ceiling and floor are generally metallic and highly reflective of electromagnetic energy. In an acoustic reverberation chamber, the walls, ceiling and floor are of a material such as concrete that is highly reflective to acoustic waves. The distribution of energy within a reverberation chamber is multimodal, with energy being transferred between modes as a consequence of reflective baffles or shaping of the room itself. Energy within the reverberation chamber may be stirred in three dimensions by a variety of methods including rotating reflective paddles or baffles, so that the stirred energy dominates the fields in the test volume. Also, variations can be obtained by rotating or moving the signal generating source or measuring device within the volume of the chamber.

FIG. 1 is a diagram of a typical electro-magnetic reverberation chamber 10 having a metallic floor 12, metallic ceiling 14, and four metallic sides 16 (only two sides shown) to enclose a device under test, DUT. In FIG. 1, a measurement antenna 20 may be mounted on a first positioner 21, and a calibration antenna 22 may be mounted on a second positioner 23. The positioners may be controlled by software and/or a user.

A line of sight, LOS, shield 24 may be mounted between the measurement antenna 20 and the calibration antenna 22. The LOS shield 24 may be metallic and used to block line of sight electric field components between the two antennas 20 and 22.

The reverberation chamber 10 may also include a horizontal z-fold tuner 26 and a vertical z-fold tuner 28. The z-fold tuners 26 and 28 may be made of large aluminum reflecting sheets supported on either a rigid box frame or a single spine and designed to provide the efficient reflecting surfaces desirable for use in the reverberation chamber 10. In particular, at one end of the vertical z-fold tuner 28 is pulley wheel 30 which rotates antenna 20 at a fixed ratio with respect to the vertical z-fold tuner 28.

SUMMARY

Embodiments described herein advantageously provide methods and systems for affecting the performance of a test chamber. According to one aspect, the performance is affected by a variable absorbing structure of the test chamber. The absorbing structure enables selective exposure of absorbing material to achieve a specific performance.

In one embodiment, the test chamber includes a reflective material and an absorbing material. The absorbing material is at least partially shielded by the reflective material. The reflective material is adjustable to expose at least a portion of the absorbing material.

One embodiment is a method of affecting performance of a reverberation chamber. The method includes positioning a variable absorbing structure within the reverberation chamber at a predetermined position and orientation to achieve a repeatable specific performance.

Another embodiment is a reverberation chamber that includes an enclosed housing and an absorbing structure having absorbing material. The enclosed housing has at least one at least partially reflective interior wall. The absorbing structure is configured to selectively expose the absorbing material to achieve a repeatable specific performance.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 3 is an illustration of a variable absorbing structure constructed in accordance with principles of the present invention;

FIG. 4 is an illustration of a variable absorbing structure constructed in accordance with principles of the present invention;

DETAILED DESCRIPTION

Figure 1:
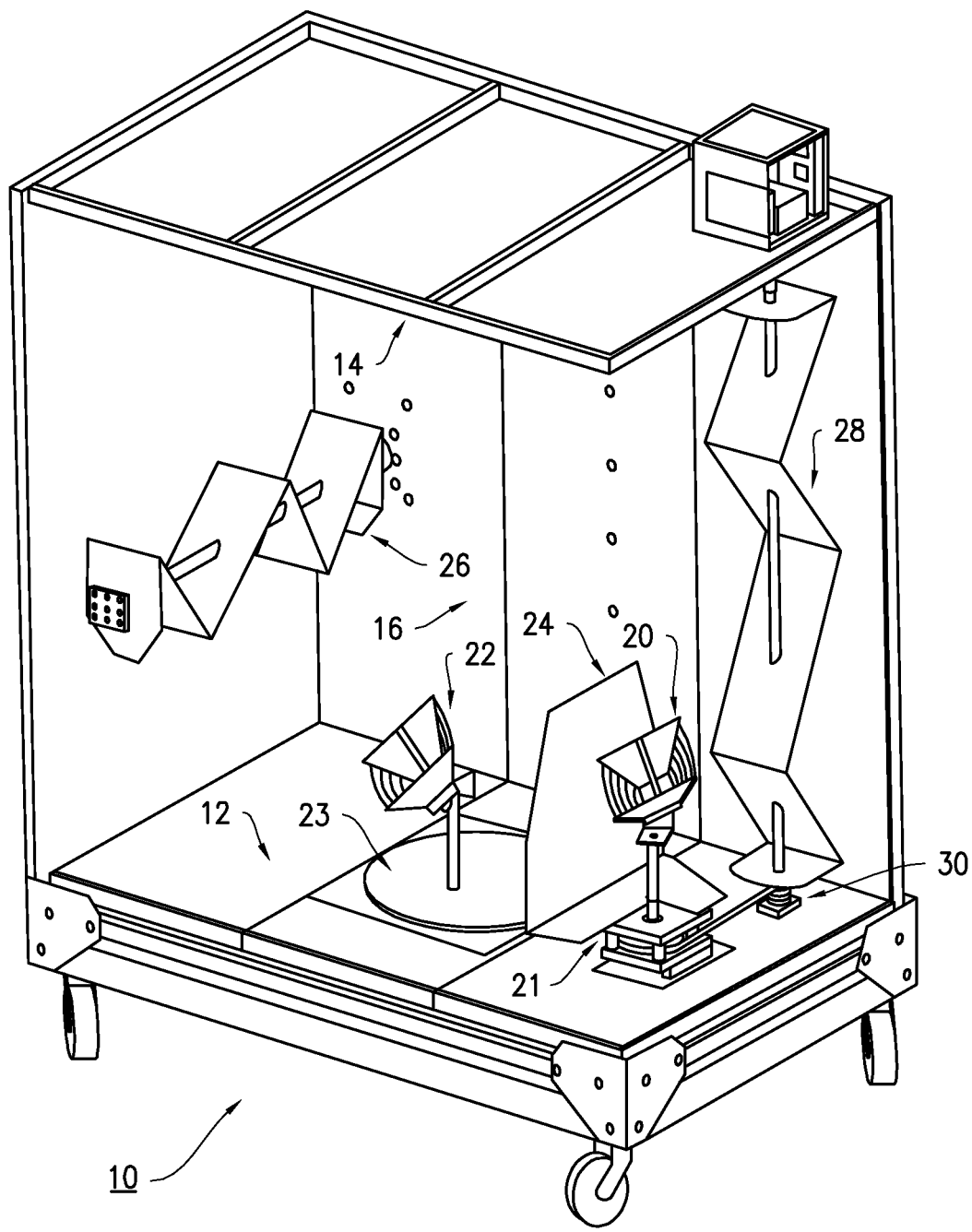
FIG. 1 is an illustration of an known electromagnetic reverberation chamber.

Before describing in detail exemplary embodiments that are in accordance with the present invention, it is noted that the embodiments reside primarily in combinations of apparatus components and processing steps related to variable loading of a test chamber. Accordingly, the system and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements.

Reverberation chambers have a wide variety of applications, and are conventionally designed with the highest Q possible. When the stirred energy dominates the fields in the test volume, the temporal signature of the transmitted waves is extremely long, resulting in a highly reverberant environment. However, in some applications, the statistical uniformity and multipath nature of the reverberant environment are desirable, but the high Q does not provide a realistic test environment to simulate desired real-world behaviors.

Figure 2:
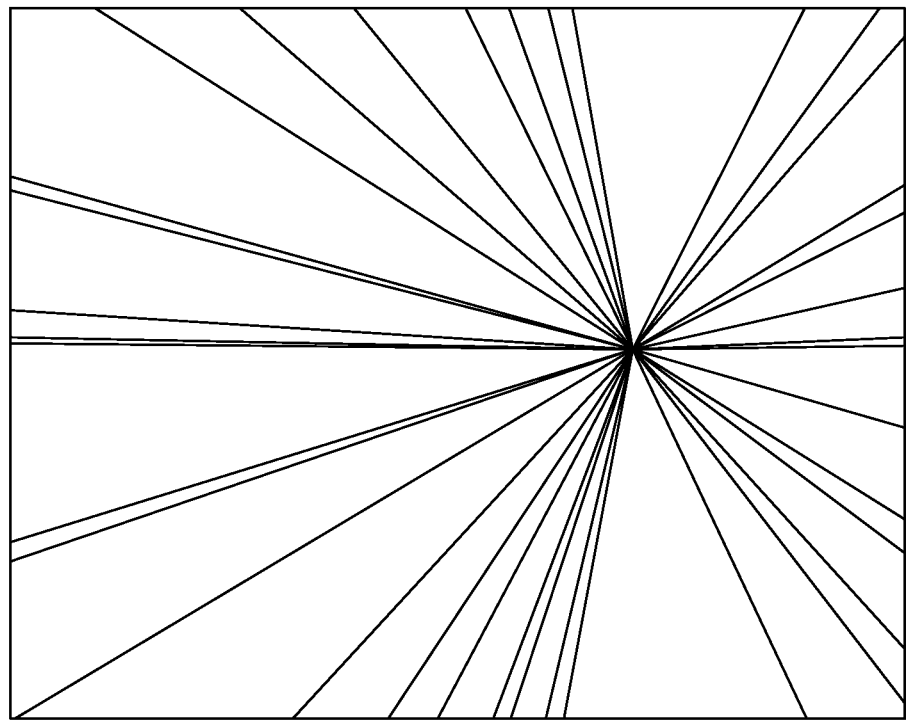
FIG. 2 is an illustration of rays arriving at one point within a reverberation chamber from some other point within the reverberation chamber.

For example, reflections produced in a reverberation chamber are assumed to be statistically uniform in both spatial and magnitude distribution. While the chamber dimensions, by design, are not identical in each direction, the loss of the surface of the cell is low enough that the probability distribution of a stirred cell can be assumed to be spherically uniform within the test volume. Such a distribution is illustrated in FIG. 2. FIG. 2 is an idealized illustration of line of sight propagation and propagation of a first few reflections of a signal propagating between two points within the chamber.

In many cases it is desirable to selectively load a reverberation chamber to achieve a desired temporal behavior, for example, an RMS delay spread. However, a device under test will load this reverberation chamber, thus making a single fixed loading impracticable for typical applications. Instead, methods and apparatus described herein for applying variable loading to a reverberation chamber while still maintaining a desired uniformity and isotropy are desirable in many applications. For example, the chamber may be loaded in all directions uniformly, or selectively loaded by absorber placed out of a line of sight between an antenna and a device under test, in order to reduce the RMS delay spread while keeping a uniform distribution within a test volume.

However, for terrestrial wireless communication, for example, the distribution of received signals in a multipath environment tends to cluster near the horizon, largely due to the propagation distances involved and the angles of incidence of direct and reflected rays within the environment. Since communication generally occurs between two points along the horizon, specular reflections off of any surface, including the earth, structures, and even interior walls, ceiling, and floors, all tend to have angles of incidence with elevations that cluster near the horizon, with little energy coming from directly above or below the radio. Only scattering reflections, usually from small and randomly placed objects (e.g. pipes, lights, etc.) are likely to produce angles of arrival within these elevations, typically with a lower magnitude, as well as probability, of those from a larger reflecting surface like the side of a building.

While the approaches described herein primarily focus on electromagnetic applications, the concepts, methods, and apparatus described herein apply to acoustic reverberation chambers as well.

Selective loading of a reverberation chamber or cell invites careful attention to placement and quantity of energy absorbing material. Desirably, selective loading of a reverberation chamber is repeatable, controllable and variable. Net energy loss within a reverberation chamber is primarily a function of surface area of the lossy material used for loading relative to the overall size and surface area of the reverberation chamber itself. Since all of the walls, baffles, and stirring paddles of a reverberation chamber have loss, the maximum Q and maximum K-factor—which is the ratio of stirred energy to unstirred energy—of the chamber is affected by the loss of these components.

A theoretical model for a reverberation chamber may include a random collection of plane waves with the uniform spherical probability distribution and the uniform magnitude and phase distribution. Such a model implies that on average, when looking in any direction from the center of the test volume, the device under test will see a uniform illumination. The test volume is a sub-volume of the volume of the test chamber. Placing an absorbing surface in such a way that there is line of sight visibility of that surface in the test volume, will result in non-uniformity of the spherical distribution and a reduction in the stirred energy. The reduction in the stirred energy may be proportional to the solid angle subtended by the absorber divided by the solid angle of a sphere ($4\pi$), and the reflectivity of the absorbing material. Alternatively, placing the absorbing surface such that it is not directly visible from within the test volume may reduce the RMS delay spread without substantially affecting uniformity of the field distribution within the test volume.

The non-uniformity that may be achieved by selectively loading a reverberation chamber may be desired in order to reproduce the non-uniform distribution seen in specific real-world environments. For example, most radio propagation in the real world is limited to a statistical distribution that peaks near the horizon, and is made up of combinations of line of sight and reflected ray paths with relatively shallow angles arising from ground bounce, ceilings and floors. Thus, it may be desirable to modify the uniform distribution of a reverberation chamber to produce a spherical probability distribution that is Gaussian or Laplacian in theta and centers near theta=90°.

To simulate a specific environmental propagation condition, corresponding to losses associated with a certain distance or propagation through walls or other lossy media, the rate of decay of the reflected signals within the reverberation chamber are desirably tuned by selective loading. By selectively loading the reverberation chamber, the RMS delay spread and overall power delay profile (PDP) can be adjusted. However, the initial RMS delay spread and PDP are a function of the physical size and loss of the unloaded reverberation chamber, and thus, the amount of loading required to produce a particular behavior varies. Further, the object to be evaluated, when placed into the test volume, affects the loading of the reverberation chamber as well. Thus, the additional loading necessary to adjust the RMS delay spread and PDP may need to be varied after the device under test is placed within the chamber.

Rather than manually adding and removing different sized pieces of absorbing material—which may lead to inconsistent results—embodiments described herein provide one or more mechanisms to continuously, controllably and repeatably vary the amount of loading in the reverberation chamber. In some embodiments, one may repeat-ably and controllably reduce RMS delay spread without altering the uniform distribution or the statistical nature of the reverberation chamber. Also, by selective loading as described herein, one may controllably vary the homogeneity and uniformity of the fields in the test volume. One may also selectively reduce the energy of given polarizations and directions within the test volume.

Returning now to the drawing figures, there is shown in FIG. 3 one embodiment of a variable absorbing structure that is position-able in a reverberation chamber to achieve repeatable, controllable, and variable loading of the reverberation chamber. FIG. 3 shows 3 different conditions of the variable absorbing structure 32, 34, 36. Element 32 is the variable absorbing structure in a fully open position. Element 34 is the variable absorbing structure in a semi-open position. Element 36 is the variable absorbing structure in a closed position. In the fully open position 32, rectangular apertures 38 expose absorbing material contained within the variable absorbing structure, thereby loading the reverberation chamber with a specific amount of loss. In the partially open position 34, the apertures 38 are partially blocked by a sliding reflective shield 40 that may be selectively adjusted to achieve a desired loading. In the fully closed position 36 the apertures 38 are completely blocked and no absorber is exposed. Note that the variable absorbing structure of FIG. 3 enables repeatability in loading the reverberation chamber, by placing the sliding reflective shield 40 in the same position and positioning the variable absorbing structure at a same position within the chamber. Note also that the loading caused by the variable absorbing structure in the chamber is very controllable via selective positioning of the sliding reflective shield 40.

Note that by controlling the placement of absorbing and reflecting surfaces within the cavity, the embodiments of FIG. 3 may be employed to absorb energy propagating within a first range of angles while reflecting energy propagating within a second range of angles. That is, certain angles of propagation will be reflected while certain other angles of propagation will be absorbed. In addition, the particular range of angles for absorption and reflection may be selected by variation of the location of the absorbing and reflecting components. This may be accomplished by covering or uncovering various portions of an absorbing surface within a larger cavity. When the angles of incidence through the apertures of the cavity align with the reflecting surface, a low loss condition occurs, while when the angles of incidence through the apertures align with the absorber, a higher loss condition occurs. The range of angles and overall performance can be controlled by the geometry of the apertures and the depth of the cavity. In addition to the mechanism used to alter the absorption angles, an additional baffle system can be used described above to vary the total amount of loss of the directional absorbing system. These parameters may be controlled to selectively restrict angles of propagation to a desired range of angles, while substantially suppressing propagation at other angles. Note also, that instead of, or in addition to, a sliding shield to variably expose the absorbing material, adjustable louvers may be employed.

Thus, the orientation and aperture size of the embodiments of FIG. 3 within the chamber may be employed to control the directivity of absorption, and consequently, the directivity of energy not absorbed. For example, the orientation of the apertures may cause selective absorption of energy propagating in one direction while not substantially absorbing energy propagating in an orthogonal direction. The rectangular shape of the apertures also enables selectivity of polarization. For example, the orientation of the apertures may cause selective absorption of polarization in one direction while not substantially absorbing polarization in an orthogonal direction.

FIG. 4 shows another embodiment of a variable absorbing structure that is positionable in a reverberation chamber to achieve repeatable, controllable, and variable loading of the reverberation chamber. Element 42 is the variable absorbing structure in a first semi-open position. Element 44 is the variable absorbing structure in a second semi-open position. Element 46 is the variable absorbing structure in a fully closed position. In the partially open position, the variable absorbing structure exposes absorbing material 48 by sliding reflective shield 50. Note that the variable absorbing structure of FIG. 4 enables repeatability in loading the reverberation chamber, by placing the sliding reflective shield 50 in the same position and positioning the variable absorbing structure of the same position within the chamber. Note also that the loading caused by the variable absorbing structure in the chamber is very controllable by way of selective positioning of the sliding reflective shield 50.

Figure 5:
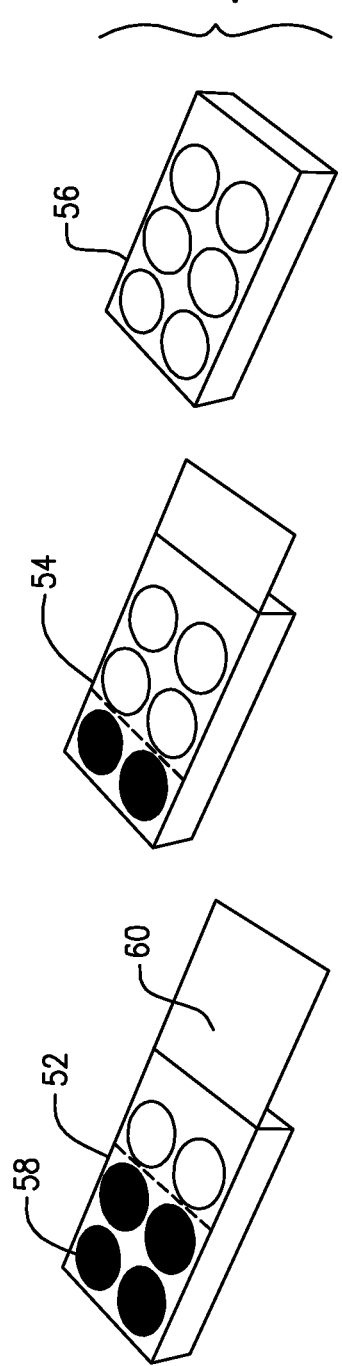
FIG. 5 is an illustration of a variable absorbing structure constructed in accordance with principles of the present invention.

FIG. 5 shows another embodiment of a variable absorbing structure that is positionable in a reverberation chamber to achieve repeatable, controllable, and variable loading of the reverberation chamber. Element 52 is the variable absorbing structure in a first semi-open position. Element 54 is the variable absorbing structure in a second semi-open position. Element 56 is the variable absorbing structure in a fully closed position. In the partially open position, the variable absorbing structure exposes absorbing material 58 by sliding reflective shield 60. Note that the variable absorbing structure of FIG. 5 enables repeatability in loading the reverberation chamber, by placing the sliding reflective shield 60 in the same position and positioning the variable absorbing structure at the same position within the chamber. Note also that the loading caused by the variable absorbing structure in the chamber is very controllable by way of selective positioning of the sliding reflective shield 60. Note further that a difference between the embodiment of FIG. 3 and the embodiment of FIG. 5 is the shape of the apertures exposing absorbing material. Shapes of the apertures other than rectangular and circular may also be employed and the shapes and sizes of the aperture may be selected to achieve a desired performance.

Note that any of the structures of FIGS. 3-5 may be built into one or more walls and/or the ceiling and/or the floor of the reverberation chamber. Thus, for example, the ceiling of the reverberation chamber may itself be constructed of a reflective material having variable apertures, as in FIG. 3, that expose absorbing material behind the apertures.

Figure 6:
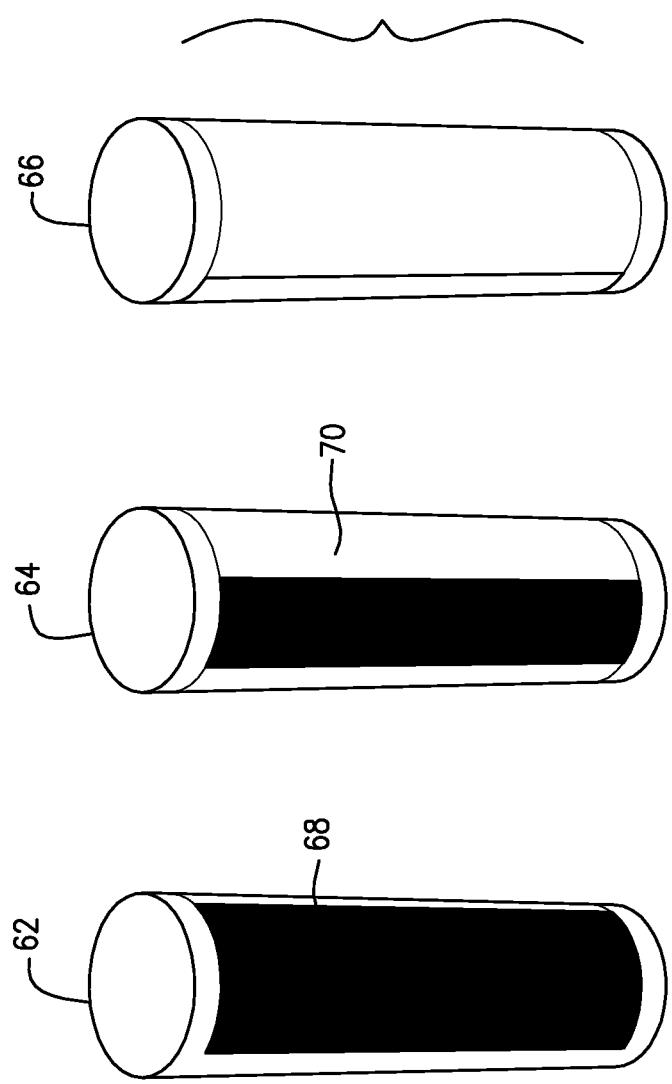
FIG. 6 is an illustration of a variable absorbing structure constructed in accordance with principles of the present invention.

FIG. 6 shows an embodiment of a cylindrical variable absorbing structure that is position-able in a reverberation chamber to achieve repeatable, controllable, and variable loading of the reverberation chamber. Element 62 is the variable absorbing structure in a first semi-open position. Element 64 is the variable absorbing structure in a second semi-open position. Element 66 is the variable absorbing structure in a fully closed position. In the partially open positions the variable absorbing structure exposes absorbing material 68 by sliding reflective shield 70. Note that the variable absorbing structure of FIG. 5 enables repeatability in loading the reverberation chamber, by placing the sliding reflective shield 70 in the same position and positioning the variable absorbing structure at the same position within the chamber. Note also that the loading caused by the variable absorbing structure in the chamber is very controllable by way of selective positioning of the sliding reflective shield 70.

Note further, that that the sliding reflective shields 40, 50, 60 and 70 may be driven by a motor that is remotely controlled by an actuator located inside or outside the reverberation chamber. Also, the sliding reflective shields may be rolled about an axis when the variable absorbing structure is fully or partially opened, thereby conserving space.

Figure 7:
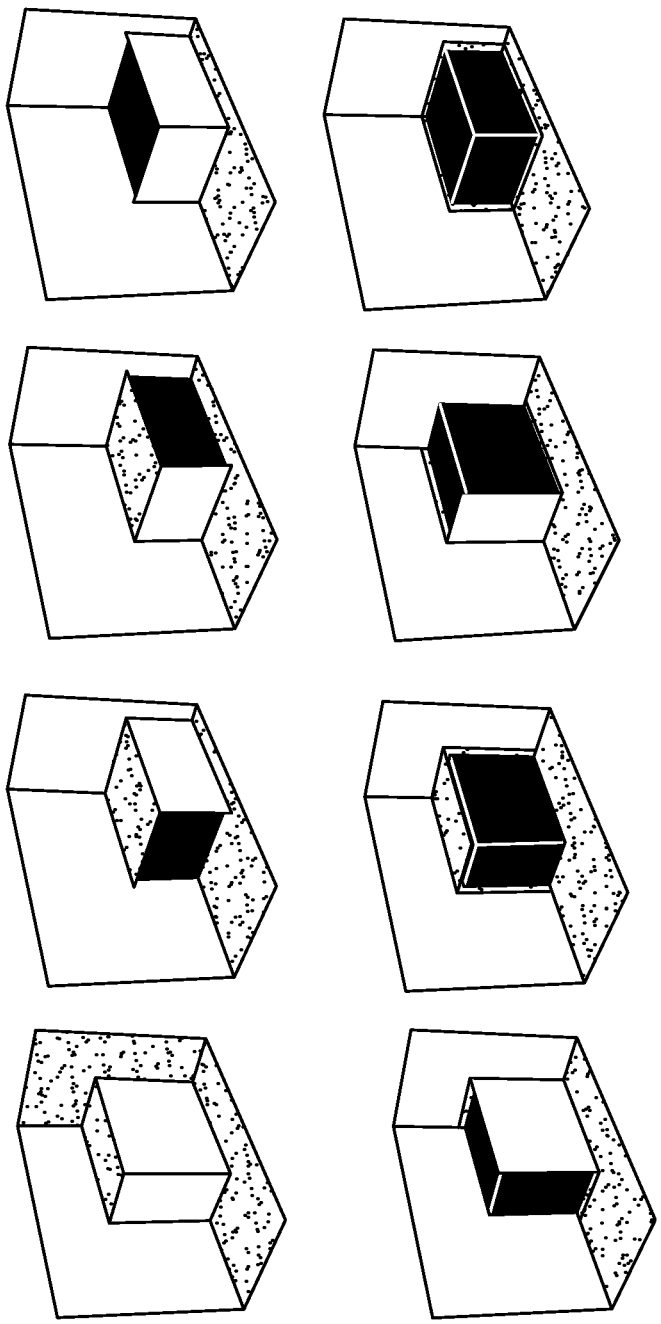
FIG. 7 is an illustration of a variable absorbing structure constructed in accordance with principles of the present invention.

FIG. 7 shows yet another embodiment of a variable absorbing structure that is positionable in a reverberation chamber to achieve repeatable, controllable, and variable loading of the reverberation chamber. The variable absorbing structure of FIG. 7 is a box shielded on three sides with absorber being exposed on the other three sides. As can be seen from FIG. 7, the variable absorbing structure can be placed in at least eight different positions to achieve different loading of the reverberation chamber.

While randomly loading the cell with lossy material can produce an RMS delay spread that is reasonable for wireless testing, random loading may or may not significantly alter the uniformity of the field structure within the chamber. Nor is random loading necessarily repeatable. In contrast, selective loading of the cell using the methods and apparatus described herein, enables repeatable reduction of RMS delay spread, repeatable control of polarization, and repeatable control of directivity, as well as repeatable control of other performance parameters.

For example, through selective loading of the cell, and control of the various dimensions, it is possible to create a test environment where the energy is primarily constrained near the azimuth plane. Thus, it may be desirable to modify the uniform distribution of a reverberation chamber to produce, for example, a spherical probability distribution that is Gaussian or Laplacian in theta and centers near theta equal to 90 degrees. The reverberation chamber modified in this way may also benefit from two dimensional stirring mechanisms that minimize the amount of energy directed into the elevation propagation directions from the azimuthal directions. As will be understood, the selective directivity in other than azimuthal directions can be achieved applying the methods and apparatus described herein.

Figure 8:
FIG. 8 is an illustration of rays in an elongated reverberation chamber.
Figure 9:
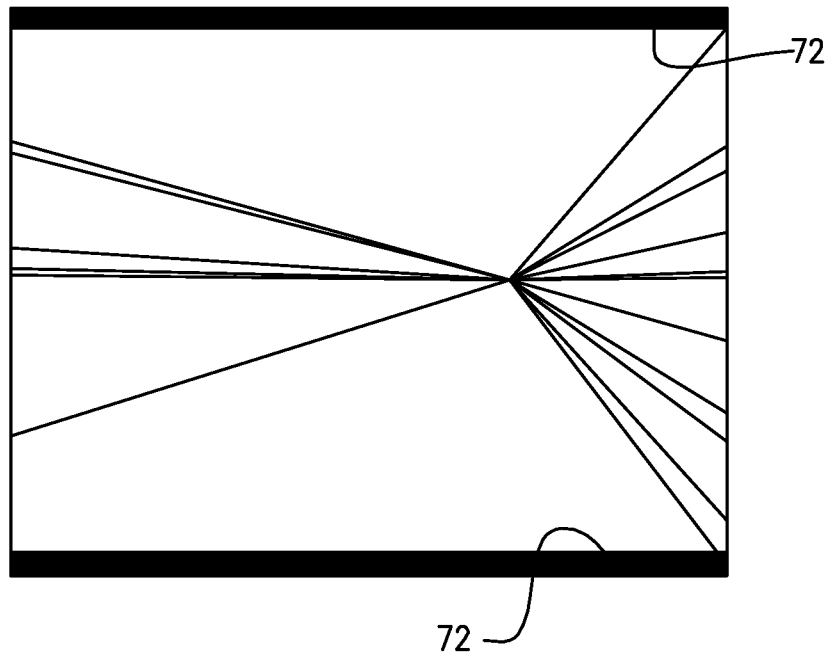
FIG. 9 is an illustration of rays in a reverberation chamber with floor and ceiling treated to reduce rays emanating at or near right angles to the floor and ceiling.

FIG. 8 shows an example of a reverberation chamber designed to alter the spatial field distribution to confine reflective rays to near horizontal. However, such a long and narrow chamber may be impractical for many applications. FIG. 9 shows that by selectively lining the top and bottom of a reverberation chamber with lossy material 72, rays bouncing off these surfaces can be weakened, thereby producing an elevation distribution clustered around the horizon. For example, the lossy material 72 may consist of absorbing material exposed by apertures formed in the top and bottom of the chamber. Thus, by using absorber and reflector treatments that produce high loss at normal angles of incidence, and that produce very low loss at shallow angles of incidence, a gradually varying distribution can be achieved.

Figure 10:
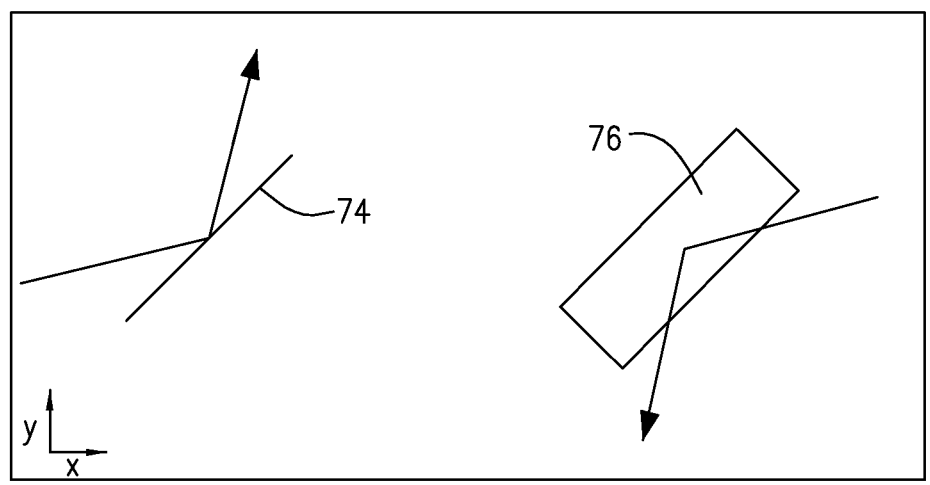
FIG. 10 is an illustration of a plan view of two and three dimensional stirrers.
Figure 11:
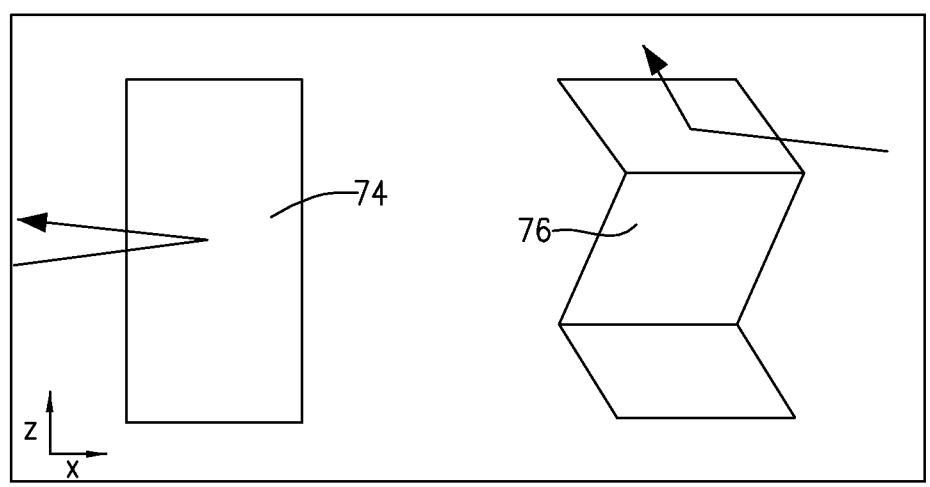
FIG. 11 is an illustration of an elevation view of two and three dimensional stirrers.

Moreover, by designing stir paddles that reflect energy primarily along the azimuth plane, 2-dimensional stirring can be achieved, minimizing the amount of energy redirected to the absorbing boundaries. FIG. 10 is a plan view of a two dimensional stirrer 74 and a three dimensional stirrer 76, and FIG. 11 is an elevation view of these two stirrers. A three dimensional stirrer moves energy between all three orthogonal modes arbitrarily with the objective of randomizing the components in each mode to produce a uniform field. Conversely, the two dimensional stirrer reflects energy between two orthogonal directions without reflecting energy into the third orthogonal direction. Note that the definition of two dimensional refers not to the geometry of the stirrer, but rather to the effect of the stirrer on the energy distribution. Thus, a paddle need not be restricted to two dimensions. For example, a paddle shaped like a plus sign (+) may be used as a two dimensional stirrer. As another example, the two dimensional stirrer may be convex. Further note that the orientation of the two-dimensional stirrer is selected based on the desired range and orientation of angles to which propagation is to be limited. For example, a two dimensional stirrer may be oriented and positioned to deflect rays at lower angles of incidence to a more horizontal direction, thereby moving energy from an undesired mode to a desired mode.

Thus, in some embodiments, a variable absorbing structure, with or without a two dimensional stirrer, is selectively positioned to substantially restrict propagation to elevations that are substantially horizontal. In some embodiments, the variable absorbing structure is selectively positioned to substantially suppress propagation above a specified elevation. More generally, in some embodiments, the variable absorbing structure is selectively positioned to substantially suppress propagation at one or more angles or a range of angles. The angle(s) or range of angles selected to be suppressed may depend on the application. Alternatively, all but a selected range of angles may be suppressed by selective placement of absorbing structure and use of one or more two-dimensional stirrers.

Some embodiments described herein include a variable absorbing structure of a test chamber. In some embodiments, the structure includes a reflective material and absorbing material at least partially shielded by the reflective material. The structure is adjustable to selectively expose at least a portion of the absorbing material. In some embodiments, the structure forms at least one of a wall, a ceiling and a floor of the test chamber. In some embodiments, the test chamber has walls, ceiling and floor that are entirely reflective, with the variable absorbing structure being placed therewithin. In some embodiments the structure may have a rectangular cross-section. For example, the structure may be a box having at least one side selectively exposing absorbing material. In some embodiments, the structure has at least one adjustable sliding shutter to selectively expose a portion of absorbing material contained within the structure. The reflective material may have apertures that are selectively exposed by adjustment of a sliding shutter. The adjustable sliding shutter may be configured to roll into a cylinder to conserve space. In some embodiments, the structure has at least one adjustable louver to selectively expose a portion of absorbing material contained within the structure. In some embodiments, the variable absorbing structure includes a cylinder. The cylinder may have a rotatable portion to selectively expose a portion of absorbing material contained within the cylinder. In some embodiments, the structure exhibits individually variable apertures having sizes selected to achieve a desired performance of the test chamber. Further, in some embodiments, the absorbing material may exhibit an absorption characteristic that varies as a function of position along a length of the absorbing material. In such embodiments, the structure may be adjustable to selectively expose absorbing material in the direction along the length of the absorbing material in which the absorption characteristic varies. And, as noted above, the structure may be adjusted by remote control to vary the loading of the reverberation chamber. In some embodiments, the structure is adjustable so that all but a selected range of angles of propagation in the test chamber are suppressed. In some embodiments, the structure is adjustable to selectively absorb a particular polarization of energy in the test chamber.

Embodiments described herein further include a method for affecting performance of a reverberation chamber. The performance is varied by positioning a variable absorbing structure within the reverberation chamber at a predetermined position and orientation to achieve a repeat-ably achievable specific performance. The method may further include adjusting a movable portion of the variable absorbing structure to vary exposure of absorbing material of the variable absorbing structure. The specific performance that may be varied may include power delay profile, RMS delay spread, Q factor, and K factor, and angular distribution. In some embodiments, the specific performance is one of a polarization selectivity and a directivity.

Some embodiments described herein include a test chamber having an enclosed housing with at least one at least partially reflective interior wall and an absorbing structure having an absorbing material. The variable absorbing structure is configured to selectively and repeat-ably vary exposure of the absorbing material to achieve a repeat-ably achievable specific performance. The variable absorbing structure may be remove-ably affixed to a surface of the housing or may be one or more walls, ceiling and/or floor of the housing. In some embodiments, the variable absorbing structure is selectively variable to absorb energy propagating within a first range of angles and to reflect energy propagating within a second range of angles. In some embodiments, the variable absorbing structure is selectively positioned to substantially restrict rays of propagation falling within a selected range of angles. In some embodiments, the variable absorbing structure is selectively positioned to substantially suppress propagation above a specified elevation. Some embodiments include a two dimensional stirrer oriented to reflect energy between two orthogonal directions without substantially reflecting energy to a third orthogonal direction.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A variable absorbing structure position-able within a reverberation chamber and configured to provide absorption of electromagnetic energy in the reverberation chamber, the structure comprising:
   reflective material configured to reflect electromagnetic energy; and
   electromagnetic absorbing material configured to absorb electromagnetic energy, the electromagnetic absorbing material at least partially shielded by the reflective material, the reflective material being adjustable relative to the absorbing material to expose a selected portion of the electromagnetic absorbing material in order to repeat-ably and selectively control an electromagnetic field distribution within the reverberation chamber.

2. The structure of claim 1, wherein the structure forms at least one of a wall, a ceiling and a floor of the reverberation chamber.

3. The structure of claim 2, wherein the structure includes a box having at least one side selectively exposing electromagnetic absorbing material.

4. The structure of claim 1, wherein the structure has at least one adjustable sliding shutter having the reflective material to selectively expose a portion of electromagnetic absorbing material of the structure.

5. The structure of claim 4, wherein the reflective material has a plurality of apertures that are selectively exposed by adjustment of at least one of the at least one adjustable sliding shutter.

6. The structure of claim 1, wherein the structure has at least one adjustable louver having the reflective material to selectively expose a portion of electromagnetic absorbing material of the structure.

7. The structure of claim 1, wherein the structure is positioned to reduce an RMS delay spread in the test chamber while substantially maintaining a uniform distribution within a test volume within the test chamber.

8. The structure of claim 1, wherein the structure includes a cylinder having the electromagnetic absorbing material.

9. The structure of claim 1, wherein the absorbing material exhibits an absorption characteristic that varies as a function of position along a length of the absorbing material.

10. The structure of claim 1, wherein the structure is adjustable so that all but a selected range of angles of propagation in the test chamber are suppressed.

11. The structure of claim 1, wherein the structure is adjustable to selectively absorb a particular polarization of energy in the test chamber.

* * * * *